(12) United States Patent
Dalbon et al.

(10) Patent No.: US 6,235,284 B1
(45) Date of Patent: May 22, 2001

(54) SYNTHETIC POLYPEPTIDES BELONGING TO THE HEPATITIS C VIRUS (HCV) AND WHICH CAN BE USED ESPECIALLY FOR DETECTING THE LATTER

(75) Inventors: Pascal Dalbon, Venissieux; Michel C. Jolivet, Bron, both of (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 08/380,160

(22) Filed: Jan. 30, 1995

Related U.S. Application Data

(63) Continuation of application No. 08/057,471, filed on May 6, 1993, now abandoned.

(30) Foreign Application Priority Data

May 6, 1992 (FR) .................................................... 92 05763

(51) Int. Cl.[7] ........................ C07K 14/02; C07K 14/005; A61K 39/29; G01N 33/543
(52) U.S. Cl. ..................................... 424/189.1; 424/186.1; 424/204.1; 424/228.1; 530/300; 530/324; 530/810; 530/388.3; 530/389.4; 436/820; 436/518
(58) Field of Search ..................................... 530/300, 324, 530/325, 326, 826, 388.3, 389.4, 402, 810; 900/220, 223; 435/5; 424/186.1, 189.1, 204.1, 228.1; 436/820, 518

(56) References Cited

U.S. PATENT DOCUMENTS 5,106,726    4/1992    Wang ........................................ 435/5

FOREIGN PATENT DOCUMENTS

| 0442394 | 2/1991 | (EP) . |
| 0484787 | 5/1992 | (EP) . |
| 0525910 | 7/1992 | (EP) . |
| WO 92/22571 | 12/1992 | (WO) . |

OTHER PUBLICATIONS

Ishida et al., J. Clin. Microbiol., 31:936–940, 1993 Harlow, "Antibodies: A Laboratory Manual", Cold Spring Harbor Laboratories, 1988, pp. 75, 76.*

Ngo et al., "Chapter 14", From: The Protein Folding Problem and Tertiary Structure Prediction, Eds Merz et al., Birkhauser, 1994, pp. 492–495.*
Rudinger, Chapter 1, From "Peptide Hormones", Ed. J.A. Parsons, pp. 1–7, University Park Press, 1976.*
M. Nasoff et al., "Identification of an Immunodominant Epitope Within the Capsid Protein of Hepatitis C Virus", *Proc. Natl. Acad. Sci. USA*, vol. 88, No. 12, pp. 5462–5466, Jun. 1991.
B. Hosein et al., "Improved Serodiagnosis of Hepatitis C Virus Infection With Synthetic Peptide Antigen from Capsid Protein,"*Proc. Natl. Acad. Sci. USA*, vol. 88, No. 9, pp. 3647–3651, May 1991.
E. Munekata et al., "Epitope–Mapping of Hepatitis C Virus Constituting Protein", *Peptide Chemistry 1990*, pp. 211–214 (1991).
J. Chiba et al., "Serodiagnosis of Hepatitis C Virus (HCV) Infection With an HCV Core Protein Molecularly Expressed By A Recombinant Baculovirus", *Proc. Natl. Acad. Sci. USA*, vol. 88, pp. 4641–4645, Jun. 1991.
G. Barany et al., The Peptides, vol. 2, pp. 1–284 (1979).
C.L. Van Der Poel et al., "Confirmation of Hepatitis C Virus Infection by New Four–Antigen Recombinant Immunoblot Assay", *The Lancet*, vol. 337, Feb. 1991.
Okamoto et al., "Enzyme–Linked Immunosorbent Assay for Antibodies Against the Capsid Protein of Hepatitis C Virus with A Synthetic Oligopeptide", *Japan, J. Exp. Med.*, vol. 60, pp. 223–233, (1990).

* cited by examiner

*Primary Examiner*—Ronald B. Schwadron
(74) *Attorney, Agent, or Firm*—Oliff & Berridge, PLC

(57) ABSTRACT

The invention relates to a polypeptide comprising a peptide sequence belonging to the sequence of the first 62 amino acids of the terminal part of the CORE (or capsid) protein of the human hepatitis C virus (HCV), the polypeptide comprising either an isolated peptide sequence that is composed of the 45 N-terminal amino acids of the core protein, with 1 to 10 amino acids optionally amputated from its N-terminal part and/or its C-terminal part, or an immunogenic sequence equivalent to the peptide sequence and exhibiting immunological cross-reactivity with the peptide sequence towards HCV. The invention also relates to a polypeptide composition, a reagent and a means for the detection of the HCV virus, a process and a device for the detection of anti-HCV antibodies, an immunotherapeutic composition and antibodies directed against HCV.

5 Claims, 2 Drawing Sheets

US 6,235,284 B1

SYNTHETIC POLYPEPTIDES BELONGING TO THE HEPATITIS C VIRUS (HCV) AND WHICH CAN BE USED ESPECIALLY FOR DETECTING THE LATTER

This is a Continuation of application Ser. No. 08/057,471 filed May 6, 1993, now abandoned.

BACKGROUND

1. Field of the Invention

The present invention generally relates to synthetic polypeptides, that is to say which are obtained by preparative routes such as chemical synthesis, composed of consecutive amino acids which are together identical to any fragment, sequence or region of the structural protein of the nucleocapsid called (SEQ ID NO:3) CORE protein (SEQ ID NO:3) of the human hepatitis C virus (HCV). These polypeptides can be used as synthetic antigens in various applications arising from their immunogenicity and which are specified below; at the forefront of these applications is the detection HCV in various body fluids such as for example a blood sample.

2. Description of Related Art

It has been established that the nucleocapsid protein or CORE protein (SEQ ID NO:3) of HCV, which is composed as established by FIG. 1 (SEQ ID NO:3) of 191 amino acids, is that which exhibits the greatest homology, on the one hand, between the sequences of the same group of viral isolates, and, on the other hand, between the different groups of viruses. Moreover, this CORE protein (SEQ ID NO:3) is encoded by a structural part of the HCV genome and therefore constitutes a structural protein. The high conservation of the structure of this protein makes it a particularly suitable candidate for the immunological detection of HCV.

Thus, the work of Hosein B, Fang C T, Popovsky M A, Ye J, Zhang M, Wang C Y, published in Improved serodiagnosis of hepatitis C virus infection with synthetic peptide antigen from capsid protein, Proc Natl Acad Sci USA 1991; 88: 3647–51, made it possible to determine an immunodominant region in the CORE protein (SEQ ID NO:3).

In conformity with a publication already mentioned, namely Hosein B, Fang C T et al., Improved serodiagnosis of hepatitis C virus infection with synthetic peptide antigen from capsid protein, Proc Natl Acad Sci USA 1991; 88: 3647–51, various synthetic peptides corresponding to certain sequences of the CORE protein (SEQ ID NO:3) can be used as antigen in detection tests in a solid phase, for example on immunoabsorbent supports.

With the same objective of immunological detection of HCV, the document EP-0,442,394 describes several polypeptides comprising a polypeptide sequence belonging to the abovementioned immunodominant region of the CORE protein.

Among the said polypeptides, the one called VIIIE, was tested in an ELISA test with respect to its immunoreactivity towards the anti-HCV antibodies contained in sera from individuals infected with HCV. This polypeptide demonstrated a good immunoreactivity towards the HCV-infected sera tested.

The substitution of such known polypeptides of the prior art, obtained by chemical synthesis, for the fusion protein corresponding to the CORE protein (SEQ ID NO:3) itself in tests of detection is advantageous since it makes it possible to reduce the risks of immunoreaction with antibodies which may be present in a sample and which are different from those directed against HCV.

However, it appeared essential to the Applicant to be able to determine a minimal and sufficient sequence for a polypeptide which, from the point of view of its antigenic properties, is equivalent to the protein in its entirety.

Indeed, the longer the peptide, the higher the risks capable of interfering with the antigenicity of the said peptide because of the higher frequency of the following events:

interference between the peptide and antibodies different from those directed against HCV by cross-reactions or between the peptide and other biological molecules present in the medium, conformational modifications relative to the structure of the native protein which may result in a disappearance of secondary and/or tertiary conformations corresponding to epitopic sites, or appearance of secondary and/or tertiary conformations different from those which the whole protein adopts, which are capable of interacting with antibodies other than the anti-HCV antibodies.

According to EP-0,442,394, the inventors have tried to shorten the length of the polypeptide VIIIE by respectively amputating 9, 19, 29 and 39 amino acids from its N-terminal part.

The immunoreactivity of each of these peptides was evaluated in ELISA tests and it is observed that the higher the number of amino acids amputated, the lower the immunoreactivity.

SUMMARY OF THE INVENTION

In contrast to these results, the present invention provides a polypeptide, or its fragments, which although consisting of an amino acid sequence much shorter than that of the VIIIE polypeptide structure manifests an immunoreactivity with all the sera of individuals or samples infected with HCV and which carry antibodies directed against the nucleocapsid protein.

The origin of the present invention is the following completely unexpected discoveries, which result from the experimental procedure outlined below:

1) an immunodominant region represented by at most the first 45 amino acids exists in the CORE protein (SEQ ID NO:3) of HCV;
2) this immunodominant region is sufficient by itself in order to obtain the same sensitivity as the total CORE protein (SEQ ID NO:3) regarding the detection of anti-HCV antibodies;
3) this immunodominant region must be continuous if it is desired to react with all the sera of individuals or blood samples infected with HCV and which possess antibodies directed against the CORE protein (SEQ ID NO:3);
4) this immunodominant region clearly contains conformational type epitopes and linear type epitopes.

Consequently, the polypeptide used in conformity with the invention comprises an isolated peptide sequence which is composed of about the 45 N-terminal amino acids of the HCV virus CORE protein (SEQ ID NO1).

Preferably, the polypeptide of the invention consists of only or of an isolated peptide sequence composed of the 45 N-terminal amino acids of the said protein or alternatively of any homologous polypeptide comprising about 45 amino acids and exhibiting an antigenic reactivity towards HCV.

Still preferably, the polypeptide of the invention consists of a peptide sequence which is composed of the N-terminal amino acids 2 to 45 of the CORE protein (SEQ ID NO:2).

DETAILED DESCRIPTION OF PREFERRED EMBODIMENTS

Figure 1:
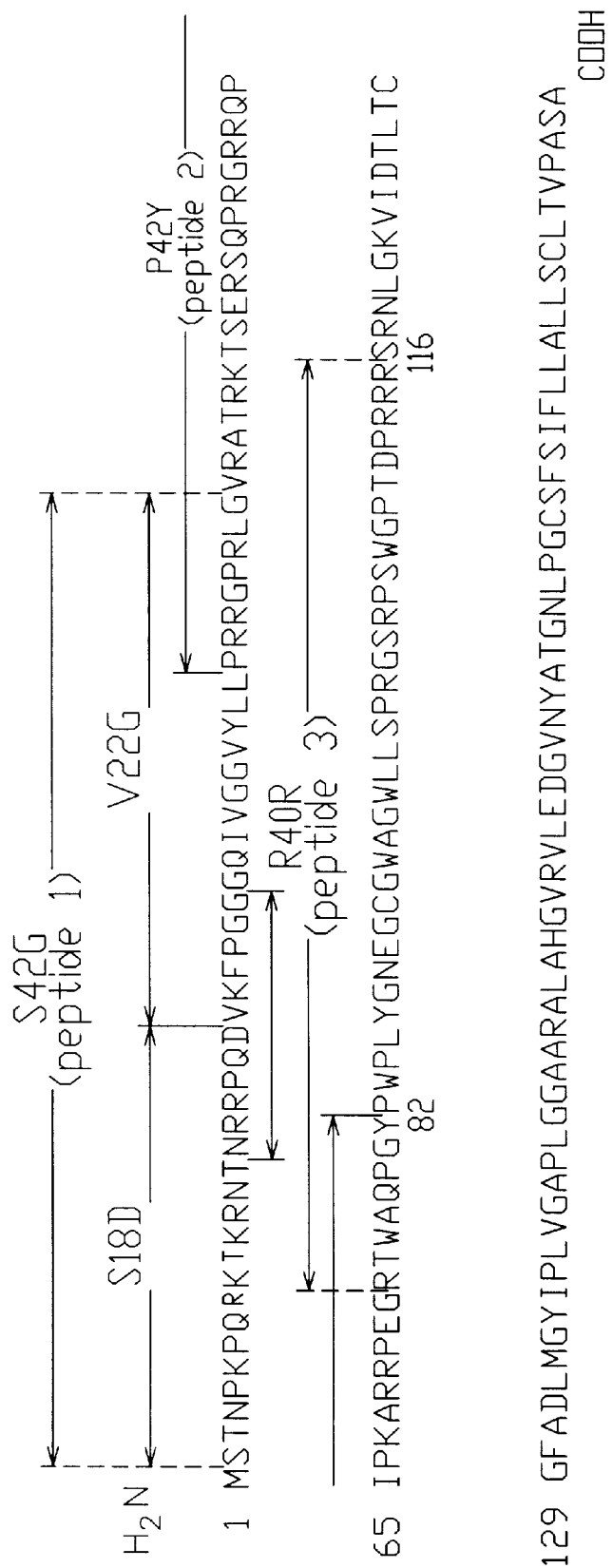
FIG. 1 depicts the CORE protein of HCV. It also depicts various peptides described herein that are fragments of the CORE protein.

The present invention arises from the experimental observations as defined below.

Firstly, the invention provides especially any one of the following polypeptide compounds or compositions:

a) only one isolated peptide sequence which is composed of 45 N-terminal amino acids of the CORE (or capsid) protein (SEQ ID NO:3) of the human hepatitis C virus (HCV), as represented in FIG. 1, 1 to 10 amino acids being optionally amputated from this sequence in its N-terminal part and/or its C-terminal part;

b) only one antigenic sequence equivalent to the peptide sequence (a), which exhibits an immunological reactivity towards anti-HCV antibodies;

c) only one sequence homologous to the peptide sequence (a), in which each constituent amino acid exhibits chemical properties identical or analogous to those of the homologous amino acid in the peptide sequence (a);

d) any appropriate mixture of the polypeptide compounds according to (a) to (c).

"Isolated peptide sequence" is understood to mean any polypeptide not fused with another protein or another peptide regardless of its route of production, for example by chemical synthesis, by lysis of the CORE protein (SEQ ID NO:3), or by genetic recombination techniques. This polypeptide can therefore be a synthetic peptide or a protein.

According to the present invention, an amino acid is said to be homologous to another amino acid when their chemical characteristics, such as polarity, hydrophobicity and/or basicity and/or acidity and/or neutrality, are essentially the same. Thus, a leucine is homologous to an isoleucine within the meaning of the above definition.

The polypeptide sequences according to the invention may be such as in the native state or modified chemically. Chemical modification is understood to mean any chemical alteration of at least one functional group of the peptide sequence which essentially preserves or even develops the biological properties of the said sequence. The replacement of an amino acid of the L series by an amino acid of the D series, a modification of the side chains of the amino acids such as an acetylation of the amine functional groups, a carboxymethylation of the thiol functional groups or an esterification of the carboxylic functional groups, or a modification of the peptide bonds such as carba, retro-inverso, reduced and methylene-oxy bonds, are especially part of the chemical modifications considered above.

The preferred amputations of the polypeptide of the invention are the amputations of respectively 6 amino acids and 11 amino acids from the N-terminal end of the CORE protein (SEQ ID NO:3).

From the above-defined peptide compounds or compositions, the invention provides a reagent for the detection of human hepatitis C virus (HCV) comprising as reactive substance any one of the abovementioned compounds or compositions and optionally any additive immunocompatible with the detection of HCV. Thus, the detection can be carried out using a polypeptide identical or analogous to those of the present invention with optionally one anti-human immunoglobulin antibody, labelled with any conventional marker such as a radioactive, fluorescent or enzymatic marker or the like. Such a reagent can be used both in a homogenous phase, for example in immunoprecipitation assays, and in a heterogenous phase, for example in immunoadsorption assays.

With the abovementioned reagent, any suitable means of detection of HCV can be obtained, whether a detection kit or any other equivalent system or unit. By way of example, the abovementioned reagent is supported on a solid support immunocompatible with the reagent as a whole; in particular, the solid support is, without limitation, in the form of a microtiter plate, a sheet, a cone, a well, a bead or any other appropriate microparticulate substrate.

The term solid support as used here includes all materials upon which the polypeptides according to the invention can be immobilized. These may be synthetic materials chemically modified or otherwise, especially polysaccharides such as cellulose materials, for example paper, cellulose derivatives such as nitrocellulose and cellulose acetate; polymers such as vinyl chloride, polyethylene, polystyrene, polyacrylate or copolymers such as vinyl chloride and propylene polymer, vinyl chloride and vinyl acetate polymer; styrene-based copolymers; natural fibers such as cotton and synthetic fibers such as nylon. Preferably, the solid support is a poly-styrene polymer, a butadiene-styrene copolymer or a butadiene-styrene copolymer mixed with one or more polymers or copolymers chosen from polystyrene, styrene-acrylonitrile or styrene-methyl methylmethacrylate copolymers, polypropylenes, polycarbonates or analogs.

Using the immunological detection reagents or means according to the invention, anti-HCV antibodies can be detected in any body part or fluid such as a blood sample of an individual suspected of being infected with HCV. For that, this body part and the abovementioned reagent simply have to be brought into contact under predetermined conditions, for example of temperature, which permit an immunological reaction where appropriate, and to then detect the presence of an immune complex with this reagent.

"Body part" is understood to mean any fluid, tissue or organ of an individual, comprising or capable of comprising anti-HCV antibodies. These body parts may be a blood, plasma or serum sample or various secretions and the like.

The process described above can be carried out in any detection device or apparatus comprising a vessel for bringing the body part analyzed into contact with a reagent as defined above, and this with means which create conditions, such as temperature, favorable for an immunological reaction where appropriate. And this device comprises means, especially optical, for the detection of the immune complex obtained with the reagent.

Another way of detecting the HCV virus using the polypeptides according to the present invention is to obtain monoclonal or polyclonal antibodies by any method known per se comprising an immunological reaction between a human or animal organism and an immunogenic agent consisting of a polypeptide composition as defined above. The antibodies thus obtained, for example conveniently labelled, can be used to detect HCV or to monitor the progression of the virus in a patient suffering from hepatitis C.

Of course, each of the polypeptide compositions according to the invention may constitute the active ingredient of an active immunotherapeutic composition, being optionally conjugated with an immunologically suitable support. A pharmaceutically acceptable excipient may supplement the said composition. Such a composition is for example a vaccinal preparation.

The immunodominant character of the peptide sequence according to the present invention was demonstrated in conformity with the following experimental procedure.

The strategy chosen consists in synthesizing long polypeptide fragments of about 40 amino acids, in the N-terminal part of the CORE protein (SEQ ID NO:3), which belong to the sequence of about the first 120 amino acids.

In a first stage, three peptides were therefore defined, beginning the synthesis at amino acid No. 2 (serine).

In conformity with FIG. 1, three peptides were synthesized, namely:

peptide called S42G (SEQ ID NO:2), extending from serine 2 up to glycine 45 peptide called P42Y (SEQ ID NO:9), extending from proline 38 up to tyrosine 81 peptide called R40R (SEQ ID NO:10), extending from arginine 74 up to arginine 115.

It appears that these peptides have some amino acids in common, which makes it possible to identify a possible antigenic determinant located at the intersection of two peptides.

The peptides were chemically synthesized by solid phase synthesis according to the Merrifield technique (Barany G, and Merrifield R. B, 1980, In the Peptides, 2, 1–284, Gross E and Meienhofer J, Eds Academic Press, New York). The practical details are those described below.

Peptide Synthesis

The peptides are synthesized on a phenylacetamidomethyl (PAM)/polystyrene/divinylbenzene resin (Applied Biosystems, Inc. Foster City, Calif.), using an automatic "Applied Biosystems 430A" synthesizer. The amino acids are coupled in the form of esters of hydroxybenzotriazole (HOBT). The amino acids used are obtained from Novabiochem (Laüflerlfingen, Switzerland) or from BACHEM (Bubendorf, Switzerland).

Chemical synthesis of the peptides was carried out using a double coupling procedure with N-methylpyrrolidone (NMP) as solvent. The peptides were simultaneously cut from their resin as well as the side protections using hydrofluoric acid (HF) in a suitable apparatus (type I cutting apparatus, Peptide Institute, Osaka, Japan).

For 1 g of peptidylresin, 10 ml of HF, 1 ml of anisble and 1 ml of dimethyl sulfide (DMS) are used, and the mixture is stirred for 45 minutes at $-2°$ C. The HF is then evaporated under vacuum. After intensive washes with ether, the peptide is eluted from the resin with 10% acetic acid and then the peptide is freeze-dried.

The peptides are purified by preparative high-performance liquid chromatography on a type C18 VYDAC column (250×21 mm) (The Separation Group, Hesperia, Calif., USA). The elution is performed with an acetonitrile gradient at a flow rate of 22 ml/min. The fractions collected are controlled by elution under isocratic conditions on an analytical C18 VYDAC column (250×4.6 mm) at a flow rate of 1 ml/min. The fractions which have the same retention time are pooled and freeze-dried. The predominant fraction is then analyzed by analytical high-performance liquid chromatography with the system described above. The peptide which is considered as being of acceptable purity results in a single peak representing 95% of the chromatogram minimum.

The purified peptides are analyzed with the objective of assessing their amino acid composition using an automatic Applied Biosystems 420 H amino acid analyzer. Measurement of the chemical molecular mass (mean) of the peptides is obtained using the L.S.I.M.S. mass spectrometer in a positive ion mode, on a dual focusing instrument VG. ZAB.ZSEQ linked to a DEC-VAX 2000 acquisition system (VG analytical Ltd, Manchester, England).

The reactivity of these three peptides towards the sera of individuals infected with the hepatitis C virus, termed (HCV) positive, was evaluated in an ELISA test according to the procedure described below.

Detection of anti-HCV Antibodies by ELISA

The wells of a microtiter plate of "NUNC MAX-ISORB™" trademark are saturated with 100 μl of a solution containing the peptide or a mixture of peptides (10 μg/ml) for 2 hours at 37° C. The plate is then emptied, then washed with a wash buffer containing 0.05% TWEEN™ 20(polysorbate 20). The wells are saturated with 100 μl of wash buffer supplemented with 10% goat serum (v/v), then incubated for 30 minutes at 37° C., then washed again as above. The sera to be analyzed are diluted to the appropriate dilution with saturation buffer. The incubation of the sera is 1 hour at 37° C. The wells are again washed. The solution of conjugate (goat IgG to human IgG labelled with peroxidase) at a dilution of 1/1000 in the saturation buffer is then added and the incubation lasts for 90 minutes at 37° C. After washing, the solution of orthophenylenediamine substrate is added. After 10 minutes, the reaction is stopped with 50 μl of $H_2SO_4$ and the optical density is read at 492 nm. It should be noted that all the tests were carried out in duplicate.

The reactivity of the peptides S42G (SEQ ID NO:2), P42Y (SEQ ID NO:9), and R40R (SEQ ID NO:10) is measured by ELISA on HCV-positive sera (P 1 to P 20 and B 1 to B 16) and on normal sera (SN 10, 11, 16, 17, 18, 19).

For that, the different peptides are adsorbed on the microplates at a concentration of 10 μg/ml and the sera are used at 1/100 dilution.

The values obtained, which are collated in Table 1 below, correspond to the optical density (OD) multiplied by $10^3$, at 492 nm.

For each serum the experiment was carried out in duplicate. The **** are values outside the upper scale.

TABLE 1

|  | S42G (SEQ ID NO: 2) | P42Y (SEQ ID NO: 9) | R40R (SEQ ID NO: 10) |
|---|---|---|---|
| P 1 | ***** | 101 | 375 |
|  | ***** | 108 | 420 |
| P 2 | ***** | 119 | 399 |
|  | ***** | 104 | 391 |
| P 3 | 2145 | 648 | 223 |
|  | 1942 | 638 | 215 |
| P 4 | ***** | 2314 | 309 |
|  | ***** | 2105 | 307 |
| P 5 | ***** | 234 | 129 |
|  | ***** | 243 | 176 |
| P 6 | 116 | 184 | 87 |
|  | 130 | 185 | 100 |
| P 7 | ***** | 2295 | 496 |
|  | ***** | 2389 | 478 |
| P 8 | ***** | 983 | 282 |
|  | ***** | 903 | 328 |
| P 9 | 186 | 238 | 159 |
|  | 163 | 231 | 158 |
| P 10 | 169 | 194 | 218 |
|  | 177 | 204 | 216 |
| P 11 | ***** | ***** | 1191 |
|  | ***** | ***** | 1377 |
| P 12 | ***** | ***** | 1121 |
|  | ***** | ***** | 1231 |
| P 13 | 114 | 64 | 113 |
|  | 106 | 108 | 116 |
| P 14 | ***** | 362 | 280 |
|  | ***** | 349 | 270 |
| P 15 | ***** | ***** | 2305 |
|  | ***** | ***** | 2335 |
| P 16 | ***** | 1742 | 938 |
|  | ***** | 1667 | 964 |
| P 17 | ***** | 799 | 217 |

TABLE 1-continued

| | S42G (SEQ ID NO: 2) | P42Y (SEQ ID NO: 9) | R40R (SEQ ID NO: 10) |
|---|---|---|---|
| P 18 | ***** | 736 | 212 |
| | ***** | 2253 | 1427 |
| | ***** | 2339 | 1327 |
| P 19 | 105 | 106 | 84 |
| | 112 | 105 | 89 |
| P 20 | ***** | 1701 | 714 |
| | ***** | 1679 | 740 |
| B 1 | ***** | 869 | 172 |
| | ***** | 811 | 173 |
| B 2 | 2302 | 1749 | 364 |
| | 2278 | 1664 | 345 |
| B 3 | 1673 | 623 | 304 |
| | 1686 | 630 | 341 |
| B 4 | ***** | 1688 | 405 |
| | ***** | 1557 | 346 |
| B 5 | ***** | 1639 | 360 |
| | 2308 | 1699 | 281 |
| B 6 | 1671 | 810 | 172 |
| | 1778 | 791 | 163 |
| B 7 | ***** | 1657 | 418 |
| | ***** | 1489 | 457 |
| B 8 | 1567 | 611 | 271 |
| | 1543 | 620 | 259 |
| B 9 | ***** | 957 | 235 |
| | ***** | 913 | 229 |
| B 10 | 360 | 227 | 108 |
| | 386 | 223 | 98 |
| B 11 | 1749 | 813 | 164 |
| | 1849 | 789 | 184 |
| B 12 | ***** | 755 | 136 |
| | ***** | 407 | 117 |
| B 13 | 1341 | 746 | 140 |
| | 1142 | 609 | 99 |
| B 14 | 455 | 248 | 130 |
| | 450 | 259 | 125 |
| B 15 | ***** | 313 | 301 |
| | ***** | 312 | 303 |
| B 16 | ***** | 222 | 117 |
| | ***** | 153 | 125 |
| SN 10 | 205 | 237 | 163 |
| | 192 | 205 | 154 |
| SN 11 | 107 | 156 | 150 |
| | 100 | 141 | 138 |
| SN 16 | 551 | 657 | 426 |
| | 537 | 667 | 439 |
| SN 17 | 129 | 156 | 104 |
| | 122 | 144 | 74 |
| SN 18 | 218 | 332 | 119 |
| | 173 | 279 | 87 |
| | 139 | 167 | 480 |
| SN 19 | 120 | 161 | 496 |

Table 1 shows that the peptides react differently with the sera.

It appears clearly that the most reactive peptide is peptide S42G (SEQ ID NO:2) which detects 31 sera out of 36.

None of these peptides detects normal sera, which confirms their specificity.

Finally, no serum which is negative with peptide S42G (SEQ ID NO:2) is positive with peptides P42Y (SEQ ID NO:9) or R40R (SEQ ID NO:10), which shows that on its own, peptide S42G (SEQ ID NO:2) detects the sera without the help of the other two peptides.

The study was then continued in order to know more precisely the antigenic determinant(s) located on peptide S42G (SEQ ID NO:2).

For this purpose, two peptides were prepared under the same conditions as above.

These two peptides are, in conformity with FIG. 1:

1) a peptide of 20 amino acids, called S18D (SEQ ID NO:11), covering sequence 2 to 21 of the CORE protein (SEQ ID NO:3)

2) a peptide of 24 amino acids, called V22G (SEQ ID NO:12), covering sequence 22 to 45 of the CORE protein.

The reactivity of these two peptides (separated and combined),was evaluated by comparing it with that of peptide S42G (SEQ ID NO:2) in an ELISA test as described above.

The reactivity of peptides S42G (SEQ ID NO:2), S18D (SEQ ID NO:11), V22G (SEQ ID NO:12), S18D (SEQ ID NO:11)+V22G (SEQ ID NO:12) is measured by ELISA on HCV-positive sera. The different peptides are absorbed onto microplates at a concentration of 10 μg/ml and the sera are used at the dilution stated.

The values obtained, which are collated in Table 2 below, correspond to the optical density at 492 nm. All the experiments were carried out in duplicate.

TABLE 2

| | SERUM | S42G (SEQ ID NO:2) | S180 + V22G (SEQ ID NO:11+ 12) | S180 (SEQ ID NO:11) | V22G (SEQ ID NO:12) |
|---|---|---|---|---|---|
| 1 | P1 1/100 | 2.500 | 0.438 | 0.012 | 0.426 |
| 2 | P2 1/100 | 2.500 | 0.310 | 0.020 | 0.290 |
| 3 | P3 1/100 | 2.500 | 0.665 | 0.162 | 0.503 |
| 4 | P4 1/100 | 2.500 | 2.500 | 0.982 | 1.739 |
| 5 | P5 1/100 | 2.500 | 2.500 | 2.500 | 2.500 |
| 6 | 1/1000 | 2.500 | 2.500 | 2.317 | 2.293 |
| 7 | 1/10000 | 2.093 | 0.977 | 0.399 | 0.578 |
| 8 | P6 1/100 | 0.000 | 0.007 | 0.007 | 0.000 |
| 9 | P7 1/100 | 2.500 | 2.500 | 2.500 | 2.500 |
| 10 | 1/1000 | 2.500 | 2.500 | 0.854 | 1.590 |
| 11 | 1/10000 | 1.916 | 0.402 | 0.165 | 0.237 |
| 12 | P8 1/100 | 2.500 | 2.500 | 2.500 | 2.241 |
| 13 | 1/1000 | 2.500 | 2.500 | 2.500 | 0.476 |
| 14 | 1/10000 | 1.565 | 0.730 | 0.681 | 0.049 |
| 15 | P9 1/100 | 0.090 | 0.027 | 0.019 | 0.008 |
| 16 | P10 1/100 | 0.172 | 0.054 | 0.028 | 0.026 |
| 17 | P11 1/100 | 2.500 | 2.500 | 0.383 | 2.500 |
| 18 | P12 1/100 | 2.500 | 2.500 | 2.500 | 2.500 |
| 19 | 1/1000 | 2.500 | 2.500 | 2.500 | 2.500 |
| 20 | 1/10000 | 2.500 | 0.560 | 0.454 | 0.106 |
| 21 | P13 1/100 | 0.000 | 0.025 | 0.012 | 0.013 |
| 22 | P14 1/100 | 2.500 | 2.500 | 0.907 | 1.778 |
| 23 | P15 1/100 | 2.500 | 2.500 | 2.500 | 1.810 |
| 24 | P16 1/100 | 2.500 | 2.500 | 0.225 | 2.500 |
| 25 | P17 1/100 | 2.500 | 2.129 | 0.297 | 1.832 |
| 26 | P18 1/100 | 2.500 | 2.500 | 2.500 | 2.500 |
| 27 | 1/1000 | 2.500 | 0.895 | 0.297 | 0.598 |
| 28 | 1/10000 | 1.006 | 0.167 | 0.095 | 0.072 |
| 29 | P19 1/100 | 0.000 | 0.021 | 0.011 | 0.010 |
| 30 | P20 1/100 | 2.500 | 2.500 | 1.433 | 2.249 |
| 31 | P21 1/100 | 2.500 | 2.383 | 0.111 | 2.272 |
| 32 | P22 1/100 | 2.500 | 2.500 | 2.500 | 2.500 |
| 33 | 1/1000 | 2.500 | 1.844 | 1.142 | 0.702 |
| 34 | 1/10000 | 0.894 | 0.234 | 0.146 | 0.088 |
| 35 | P23 1/100 | 0.000 | 0.030 | 0.015 | 0.015 |
| 36 | P24 1/100 | 2.500 | 0.594 | 0.015 | 0.579 |
| 37 | P25 1/100 | 2.500 | 2.500 | 2.500 | 2.252 |
| 38 | 1/1000 | 2.500 | 2.500 | 2.199 | 0.695 |
| 39 | 1/10000 | 1.550 | 0.418 | 0.329 | 0.089 |
| 40 | P26 1/100 | 2.500 | 2.500 | 2.500 | 2.500 |
| 41 | 1/1000 | 2.500 | 2.500 | 2.500 | 1.541 |
| 42 | 1/10000 | 2.500 | 1.156 | 0.957 | 0.199 |
| 43 | P27 1/100 | 2.500 | 2.500 | 1.425 | 1.600 |
| 44 | P28 1/100 | 2.500 | 2.500 | 0.115 | 2.500 |
| 45 | P29 1/100 | 0.331 | 0.005 | 0.000 | 0.005 |
| 46 | P30 1/100 | 2.500 | 2.500 | 0.483 | 2.500 |
| 47 | P31 1/100 | 2.500 | 2.500 | 2.500 | 2.500 |
| 48 | 1/1000 | 2.500 | 2.500 | 1.975 | 2.500 |
| 49 | 1/10000 | 2.071 | 1.030 | 0.183 | 0.847 |
| 50 | P32 1/100 | 2.500 | 2.500 | 1.046 | 1.639 |
| 51 | P33 1/100 | 2.500 | 2.500 | 1.307 | 1.987 |
| 52 | P34 1/100 | 2.500 | 2.500 | 2.500 | 1.618 |
| 53 | P35 1/100 | 2.500 | 2.500 | 2.500 | 1.504 |
| 54 | P36 1/100 | 2.500 | 1.341 | 0.115 | 1.226 |
| 55 | P37 1/100 | 2.500 | 2.500 | 2.500 | 2.500 |

TABLE 2-continued

| SERUM | | S42G (SEQ ID NO:2) | S180 + V22G (SEQ ID NO:11+ 12) | S180 (SEQ ID NO:11) | V22G (SEQ ID NO:12) |
|---|---|---|---|---|---|
| 56 | 1/1000 | 2.500 | 1.388 | 0.523 | 0.865 |
| 57 | 1/10000 | 1.088 | 0.230 | 0.102 | 0.128 |
| 58 | P38 1/100 | 2.500 | 2.500 | 2.500 | 2.500 |
| 59 | 1/1000 | 2.500 | 2.335 | 0.753 | 1.582 |
| 60 | 1/10000 | 1.477 | 0.156 | 0.099 | 0.057 |
| 61 | P39 1/100 | 2.500 | 2.500 | 2.500 | 1.835 |
| 62 | P40 1/100 | 2.500 | 2.500 | 2.500 | 2.500 |
| 63 | P41 1/100 | 2.500 | 2.500 | 1.579 | 2.218 |
| 64 | P42 1/100 | 0.034 | 0.000 | 0.000 | 0.000 |
| 65 | CTS 1/100 | 2.500 | 2.500 | 2.500 | 2.500 |
| 66 | 1/1000 | 2.500 | 2.500 | 2.500 | 1.155 |
| 67 | 1/10000 | 2.500 | 0.338 | 0.295 | 0.043 |
| 68 | 1/100 | 2.500 | 2.500 | 2.500 | 2.500 |
| 69 | 1/1000 | 2.500 | 2.500 | 2.500 | 1.605 |
| 70 | 1/10000 | 1.336 | 0.602 | 0.347 | 0.255 |
| 71 | B1 1/100 | 2.500 | 2.500 | 1.859 | 1.225 |
| 72 | B2 1/100 | 2.500 | 2.500 | 1.781 | 0.756 |
| 73 | B3 1/100 | 2.500 | 1.573 | 1.244 | 0.329 |
| 74 | B4 1/100 | 2.500 | 2.500 | 2.500 | 2.500 |
| 75 | 1/1000 | 2.500 | 2.464 | 1.250 | 1.214 |
| 76 | 1/1000 | 1.021 | 0.315 | 0.171 | 0.144 |
| 77 | B5 1/100 | 2.500 | 2.500 | 2.032 | 0.863 |
| 78 | B6 1/100 | 2.500 | 2.500 | 2.500 | 0.749 |
| 79 | B7 1/100 | 2.500 | 2.500 | 2.500 | 2.102 |
| 80 | B8 1/100 | 2.500 | 1.720 | 1.362 | 0.358 |
| 81 | B9 1/100 | 2.500 | 2.500 | 0.808 | 2.082 |
| 82 | B10 1/100 | 0.721 | 0.324 | 0.099 | 0.225 |
| 83 | B11 1/100 | 2.084 | 2.500 | 2.324 | 0.616 |
| 84 | B12 1/100 | 2.500 | 2.392 | 1.375 | 1.017 |
| 85 | B13 1/100 | 1.809 | 0.674 | 0.370 | 0.304 |
| 86 | B14 1/100 | 0.698 | 0.258 | 0.072 | 0.186 |
| 87 | B15 1/100 | 2.500 | 1.044 | 0.090 | 0.954 |
| 88 | B16 1/100 | 2.500 | 2.500 | 2.500 | 2.500 |

Each serum was, in a first instance, tested at the dilution 1/100. In the event where the response proved saturating (value 2500) for all the peptides (example: serum P 5) a 1/1000 dilution, and if necessary a 1/10,000 dilution, was carried out.

It appears that for all the HCV-positive sera, the reactivity of peptide S42G (SEQ ID NO:2) is substantially greater than the reactivity of peptides S18D (SEQ ID NO:11) and V22G (SEQ ID NO:12), and than that of S18D (SEQ ID NO:11)+ V22G (SEQ ID NO:12).

The sera P6, P9, P10, P13, P19, P23, P24 are sera which do not possess antibodies against the CORE protein (SEQ ID NO:3) of HVC.

Although these results as a whole are unambiguous, the attachment of the different peptides to the wells of the microtiter plates can modify the epitopes or determinants of the peptide tested. The plates used (NUNC MAXISORB™) are polystyrene plates irradiated with gamma rays, which bind the peptides in a noncovalent manner via electrostatic type bonds but also hydrophobic bonds. It is possible that peptides, depending on their sequence, are selectively adsorbed, thus favoring a well defined part and thus preventing immunogenic reactivity towards another part which may have become less acceptable.

To evaluate this hypothesis, inhibition tests, whose usefulness lies in the fact that they allow the formation of the antigen-antibody complex in liquid medium, were carried out, thus dispensing with possible artifacts linked to the adsorption of peptides onto a solid support.

The methodology is that described below.
Inhibition Test

The inhibition experiments were carried out by reaction, in liquid phase, of the HCV sera with the peptides followed by reaction of the remaining antibodies with the peptide adsorbed onto the microplates. The inhibitory peptides are incubated at a concentration of 0.1 mg/ml with sera of appropriate dilution. The rest of the manipulation is identical to that described for the ELISA test.

Peptide S18D (SEQ ID NO:11), or V22G (SEQ ID NO:12), or a mixture of both, is preincubated overnight in the presence of the serum to be tested. The antibodies can bind onto the corresponding sites. The mixture (peptide+ serum) is then incubated with the peptide S42G (SEQ ID NO:2) adsorbed onto the microtiter plates. If all the antibodies reacted during the incubation with the peptides S18D (SEQ ID NO:11), V22G (SEQ ID NO:12), or with the mixture, no reactivity will be observed, which will result in a 100% inhibition. In contrast, if antibodies specific for peptide S42G (SEQ ID NO:2) remain, they will then be able to react.

A control is carried out by preincubating each serum with peptide S42G (SEQ ID NO:2), which makes it possible to calculate the percentage inhibition.

Table 3 collates the results of the inhibition of the binding of anti-HCV antibodies (dilution 1/10,000) onto peptide S42G (SEQ ID NO:2), by preincubation of HCV sera with peptide S42G (SEQ ID NO:2), peptide S18D (SEQ ID NO:11), peptide V22G (SEQ ID NO:12) and the mixture of peptides S18D (SEQ ID NO:11)+S22G.

TABLE 3

| | serum | inhibition S42G (SEQ ID NO:2) | inhibition S18D (SEQ ID NO:11) | inhibition V22G (SEQ ID NO:12) | inhibition pool S18D + V22G (SEQ ID NOS:11 + 12) |
|---|---|---|---|---|---|
| 1 | P5 | 100% | 3.5% | 83.0% | 77.0% |
| 2 | P7 | 100% | 8.4% | 81.0% | 86.0% |
| 3 | P8 | 100% | 1.4% | 77.4% | 53.0% |
| 4 | P18 | 100% | 10.6% | 48.0% | 52.0% |
| 5 | P22 | 100% | 6.6% | 65.5% | 57.0% |
| 6 | P25 | 100% | 14.1% | 71.8% | 70.0% |
| 7 | P31 | 100% | 2.0% | 39.9% | 27.0% |
| 8 | P37 | 100% | 43.6% | 88.7% | 73.0% |
| 9 | P38 | 100% | 8.9% | 70.3% | 65.0% |
| 10 | B4 | 100% | 16.8% | 83.6% | 72.0% |

As shown in Table 3, no peptide completely inhibits the reactivity of the sera towards peptide S42G (SEQ ID NO:2).

In other words, this experiment proves that antibodies specific for peptide S42G (SEQ ID NO:2) exist which do not react with either peptide S18D (SEQ ID NO:11) or with peptide V22G (SEQ ID NO:12), the sum of both representing the total sequence of peptide S42G (SEQ ID NO:2).

A final hypothesis to be evaluated consists in verifying that the antibodies specific for peptide S42G (SEQ ID NO:2) were not directed against the central part of peptide S42G (SEQ ID NO:2), that is to say at the junction of peptides S18D (SEQ ID NO:11) and V22G (SEQ ID NO:12).

A peptide was therefore prepared (cf FIG. 1) whose sequence comprises the C-terminal part (6 amino acids) of peptide S18D (SEQ ID NO:11) and the N-terminal part (6 amino acids) of peptide V22G (SEQ ID NO:12).

Although this peptide exhibits reactivity with HCV-positive sera, the level obtained is in no case comparable to that obtained with peptide S42G (SEQ ID NO:2).

The set of results presented above makes it possible to draw the following conclusions.

In the 120 N-terminal amino acids of the CORE protein (SEQ ID NO:3), and more particularly in the first 62 amino acids, the first 45 amino acids are the most reactive towards HCV-positive sera.

The first 21 amino acids (peptide S18D (SEQ ID NO:11)) react, which shows the presence of one or more antigenic determinants on this peptide.

The amino acids 22 to 45 (peptide V22G (SEQ ID NO:12)) also carry one or more epitopes.

The junction of these two sequences is also reactive.

Consequently, the sequence 1–45 of the CORE protein (SEQ ID NO:3) is pluriepitopic.

Furthermore, one or more antigenic determinants exist which are reactive only insofar as the entire sequence 2–45 is available and not in a discontinuous manner (peptides S18D (SEQ ID NO:11) +V22G (SEQ ID NO:12)). These epitopes, which are specific to peptide S42G (SEQ ID NO:2), are without any doubt conformational type epitopes which can exist only insofar as this sequence of 44 amino acids (peptide S42G (SEQ ID NO:2)) has a suitable structure, a structure which is not obtained with smaller-sized peptides.

If the amino acid sequence of peptide S42G (SEQ ID NO:2) should not be discontinuous in order to preserve all the epitopes, it can be asked if the N- and/or C-terminal parts of peptide S42G (SEQ ID NO:2) are involved in the epitopic conformations of S42G (SEQ ID NO:2) or carry the epitopes themselves.

In order to try to respond, five peptide fragments derived from S42G (SEQ ID NO:2) by N- and/or C-terminal amputations were defined.

Figure 2:
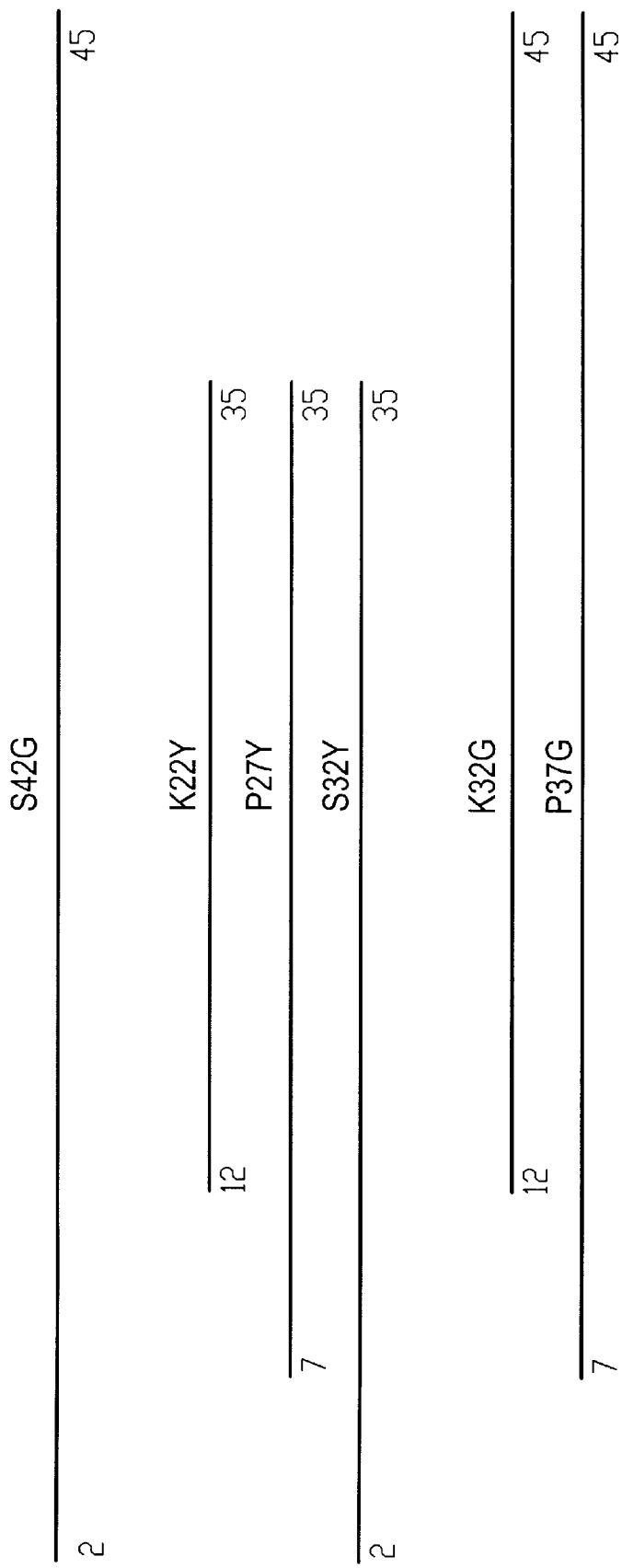
FIG. 2 depicts the peptide S42G and five fragments thereof that were synthesized in accordance with the Merrifield technique.

In conformity with FIG. 2, the following five fragments were synthesized according to the Merrifield technique in conformity with the procedure described above:

peptide called P37G (SEQ ID NO:8) corresponding to the amino acid sequence 7 to 45 of the CORE protein (SEQ ID NO:3) and to an amputation of 5 amino acids from the N-terminal part of S42G (SEQ ID NO:2), peptide called K32G (SEQ ID NO:7) corresponding to the amino acid sequence 12 to 45 of the CORE protein (SEQ ID NO:3) and to an amputation of 10 amino acids from the N-terminal part of S42G (SEQ ID NO:2), peptide called S32Y (SEQ ID NO:6) corresponding to the amino acid sequence 2 to 35 of the CORE protein (SEQ ID NO:3) and to an amputation of 10 amino acids from the C-terminal part of S42G (SEQ ID NO:2), peptide called P27Y (SEQ ID NO:5) corresponding to the amino acid sequence 7 to 35 of the CORE protein (SEQ ID NO:3) and to an amputation of 5 amino acids from the N-terminal part and of 10 amino acids from the C-terminal part of S42G (SEQ ID NO:2), peptide called K22Y (SEQ ID NO:4) corresponding to the amino acid sequence 12 to 35 of the CORE protein and to an amputation of 10 amino acids from the N-terminal part and of 10 amino acids from the C-terminal part of S42G (SEQ ID NO:2).

The reactivity of the five peptides towards sera of individuals infected with HCV was evaluated in ELISA tests in conformity with the procedure described above for measuring the activity of the peptides S42G (SEQ ID NO:2), P42Y (SEQ ID NO:9) and R40R.

Table 4 below collates the results obtained for the peptides S42G (SEQ ID NO:2), S32Y, P27Y (SEQ ID NO:5), K22Y in order to examine the influence of an amputation of the N-terminal part and the C-terminal part of the peptide S42G (SEQ ID NO:2).

These results are expressed in optical density values read at 492 nm multiplied by a factor of $10^3$.

TABLE 4

| Serum | Dilution | RIBA C22 | (SEQ ID NO: 2) S42G | (SEQ ID NO: 6) S32Y | (SEQ ID NO: 5) P27Y | (SEQ ID NO: 4) K22Y |
|---|---|---|---|---|---|---|
| P 1 | 1/100 | | D | 703 | 620 | 435 |
| P 2 | 1/100 | | D | 1177 | 891 | 666 |
| P 3 | 1/100 | | D | 1576 | 1470 | 1031 |
| P 23 | 1/100 | | 146 | 157 | 138 | 125 |
| P 10 | 1/100 | | 56 | 78 | 60 | 66 |
| P 17 | 1/100 | | D | D | 2300 | 1930 |
| P 24 | 1/100 | | D | 1214 | 1063 | 735 |
| P 29 | 1/100 | | 594 | 400 | 347 | 310 |
| P 30 | 1/100 | | D | D | 2274 | 1805 |
| P 32 | 1/100 | | D | D | D | D |
| B 3 | 1/100 | | D | D | D | 2033 |
| P 4 | 1/100 | | D | D | D | D |
|  | 1/1000 | | D | 2165 | 2111 | 1959 |
|  | 1/10,000 | | 588 | 369 | 324 | 300 |
| P 5 | 1/100 | | D | D | D | D |
|  | 1/1000 | | D | D | D | D |
|  | 1/10,000 | | 1880 | 1242 | 856 | 394 |
| P 7 | 1/100 | | D | D | D | D |
|  | 1/1000 | | D | D | D | D |
|  | 1/10,000 | | 2024 | 1932 | 1667 | 1487 |
| P 8 | 1/100 | | D | D | D | D |
|  | 1/1000 | | D | D | D | 2257 |
|  | 1/10,000 | | 1423 | 1068 | 654 | 335 |
| P 14 | 1/100 | | D | D | D | D |
|  | 1/1000 | | D | D | D | D |
|  | 1/10,000 | | 1296 | 601 | 566 | 398 |
| P 16 | 1/100 | | D | D | D | D |
|  | 1/1000 | | D | 983 | 913 | 610 |
|  | 1/10,000 | | 750 | 124 | 104 | 75 |
| A 8 | 1/100 | 4 | D | D | D | D |
|  | 1/1000 | | D | 1372 | 1198 | 431 |
|  | 1/10,000 | | 620 | 173 | 118 | 56 |
| A 9 | 1/100 | 4 | D | D | D | 2152 |
|  | 1/1000 | | D | 1941 | 1388 | 282 |
|  | 1/10,000 | | 394 | 297 | 182 | 43 |
| A 10 | 1/100 | 4 | D | D | 2308 | 2114 |
|  | 1/1000 | | D | 373 | 334 | 207 |
|  | 1/10,000 | | 819 | 33 | 31 | 26 |
| A 11 | 1/100 | 4 | D | 2240 | 1937 | 1878 |
|  | 1/1000 | | 1865 | 228 | 226 | 212 |
|  | 1/10,000 | | 223 | 36 | 33 | 31 |
| A 12 | 1/100 | 4 | D | D | D | D |
|  | 1/1000 | | D | D | D | 646 |
|  | 1/10,000 | | 848 | 588 | 365 | 62 |

The sera P23 and P10, are sera which do not possess antibodies against the CORE protein (SEQ ID NO:3) of HCV.

From this Table, it can be deduced that when the 10 amino acids of its C-terminal part are amputated, S42G (SEQ ID NO:2) loses its reactivity and that furthermore if 5 and 10 amino acids are respectively amputated from its N-terminal part, this results in a reduction in immunoreactivity which increases as a function of decreasing peptide length. (cf FIG. 2, and in particular the sera P2, P5 and P8 of Table 4).

Table 5 collates the results of the tests of immunoreactivity of the peptides S42G (SEQ ID NO:2), P37G (SEQ ID NO:8), K32G (SEQ ID NO:7), during ELISA tests, to examine the influence of amputation of the N-terminal part of peptide S42G (SEQ ID NO:2).

The values given correspond to the optical density read at 492 nm multiplied by the factor $10^3$.

TABLE 5

| Serum | Dilution | SEQ ID NO:2 S42G | SEQ ID NO:8 P37G | SEQ ID NO:9 K32G |
|---|---|---|---|---|
| A8 | 1/1000 | D | D | D |
|  | 1/10,000 | 921 | 525 | 666 |
| A9 | 1/1000 | D | 2059 | 1675 |
|  | 1/10,000 | 672 | 275 | 229 |
| A10 | 1/10,000 | 1485 | 1215 |  |
| A11 | 1/1000 | D | D | 2108 |
|  | 1/10,000 | 397 | 321 | 343 |
| A12 | 1/1000 | D | D | D |
|  | 1/10,000 | 1418 | 823 | 598 |
| A13 | 1/1000 | D | D | D |
|  | 1/10,000 | 1519 | 1061 | 1247 |
| A14 | 1/1000 | 1407 | 539 | 998 |
|  | 1/10,000 | 149 | 65 | 103 |
| A15 | 1/1000 | D | D | D |
|  | 1/10,000 | 1357 | 905 | 715 |
| A16 | 1/1000 | D | D | D |
|  | 1/10,000 | D | 2003 | D |
| A19 | 1/1000 | D | D | D |
|  | 1/10,000 | 620 | 446 | 594 |
| A20 | 1/1000 | D | D | D |
|  | 1/10,000 | D | 2338 | D |
| A21 | 1/1000 | 1319 | 652 | 993 |
|  | 1/10,000 | 177 | 90 | 123 |
| A22 | 1/1000 | 1216 | 702 | 876 |
|  | 1/10,000 | 164 | 102 | 129 |
| A23 | 1/1000 | D | D | D |
|  | 1/10,000 | 860 | 557 | 774 |

These results strengthen us regarding the hypothesis according to which peptide S42G (SEQ ID NO:2) must be present in its entire sequence from 2 to 45 in order to exhibit maximum immunoreactivity.

In all cases, S42G (SEQ ID NO:2) is higher than P37G (SEQ ID NO:8), which indicates that the 5 N-terminal amino acids play a role in the antigenicity.

However, in certain cases, little or no difference is observed in reactivity between peptides P37G (SEQ ID NO:8) and K32G (SEQ ID NO:7), which would tend to prove that amino acids 7 to 11 are not of major importance for the antigenicity of peptide S42G (SEQ ID NO:2).

Moreover, a comparison of Tables 4 and 5 makes it possible to demonstrate the importance of the 10 C-terminal amino acids of peptide S42G (SEQ ID NO:2) in the immunoreactivity itself.

Finally, the entire CORE protein (SEQ ID NO:3) (191 amino acids) was replaced by peptide S42G (SEQ ID NO:2) (44 amino acids), to detect the anti-HCV antibodies.

For this, the choice was made to compare the sensitivity of peptide S42G (SEQ ID NO:2) to that of the 2nd generation ORTHO HCV ELISA test; it is a test marketed by the company ORTHO which comprises a fusion protein incorporating the CORE protein (SEQ ID NO:3) of HCV, called C22-3; cf Vanderpoel, C. L., HTM Cuypers, H. W Reesink et al., 1991, Confirmation of hepatitis C virus infection by new four antigen recombinant immunoblot assay, Lancet 337; 317–319.

The comparison was carried out on 173 samples which were positive with the 2nd generation ORTHO HCV ELISA test.

Of 173 samples, the peptide S42G (SEQ ID NO:2) detected 151 of them, which gives a sensitivity of 87.28%. The 22 discordant sera were then analyzed using another 2nd generation test, namely CHIRON RIBA HCV. It is an immunoblotting intended for the detection of antibodies directed against the hepatitis C virus antigens in human serum or plasma. This test comprises five recombinant antigens (proteins). One of them is the recombinant CORE protein C22-3 obtained in the form of a fusion protein with human superoxide dismutase and expressed by a yeast.

It is found at the end of this confirmatory test that none of the 22 sera exhibits reactivity towards the band C22-3 (CORE).

Consequently, the sensitivity of peptide S42G (SEQ ID NO:2) is 100% relative to the CORE protein (C22-3) of the 2nd generation CHIRON RIBA HCV test.

In conclusion, the CORE protein (SEQ ID NO:3) can be replaced by the peptide S42G (SEQ ID NO:2) for the serological detection of HCV.

At this stage of the description of the invention, it is appropriate to demonstrate the advantageous use of synthetic peptides relative to that of recombinant protein fragments. For that, the results and experimental observations according to the invention were compared with those of the publication, namely: Nasoff M S, Zebedee S L, Inchauspe G, Prince A M, Identification of an immunodominant epitope within the capsid protein of hepatis [sic] C virus, Proc Natl Acad Sci USA 1991; 88: 4641–5. This publication relates to the production of recombinant protein fragments of the CORE protein (SEQ ID NO:3) expressed in *E. coli*, and reports results which are both similar to and different from those reported above.

Indeed, the authors have expressed a recombinant protein comprising the first 74 amino acids of the CORE protein (SEQ ID NO:3). The cloning strategy used results in the production of fusion proteins. In other words, the 74 N-terminal amino acids of the HCV CORE protein (SEQ ID NO:3) are preceded by 308 amino acids of which the first 221 correspond to glutathione S-transferase. The reactivity of this protein of 382 amino acids, of which only 20% represent the CORE protein (SEQ ID NO:3), towards HCV-positive sera is good only in appearance given the very small number of sera tested (5 human sera).

In contrast, a protein comprising the sequence 69–120 of the CORE protein (SEQ ID NO:3), exhibits no reactivity towards these same sera. This last result is in relative contradiction with those of the present invention since the peptide R40R (SEQ ID NO:10) which comprises the sequence 75–116 of this same protein reacts nevertheless with some sera (about 10%, cf Table 1).

These same authors pursued their work, producing other recombinant fusion proteins.

Number of human sera (9 sera), show that one sequence reacts better than another sequence. A third sequence exhibits for its part no reactivity. This last result is also in relative contradiction with those presented according to the invention since the peptide P42Y (SEQ ID NO:9) (amino acids 39–82) exhibits (cf Table 1) a high reactivity although less than the peptide S42G (SEQ ID NO:2).

Furthermore, another publication, namely: Okamoto H, Munekata E, Tsuda F, Takahashi K, Yotsumoto C, et al., 1990, Jpn, J. Exp Med 60, 223–233, has shown that a eptide of 36 amino acids reacts with at least 70% of HCV-positive sera.

The results obtained according to the invention are not in agreement with the results of these authors since it has been demonstrated that in all the cases of HCV sera studied (cf Table 2), the reactivity of the peptide S42G (SEQ ID NO:2) (sequence 2–45) is substantially greater than that of the peptides S18D (SEQ ID NO:11) (sequence 2–21) and V22G (SEQ ID NO:12) (sequence 22–45).

The explanation proposed to explain these divergent results relates to the production of different fragments of the CORE protein (SEQ ID NO:3) in both cases.

According to the invention, the peptides obtained by chemical synthesis comprise only the sequence mentioned for each of them, and as explained above, this is one of the advantages linked to these synthetic peptides.

In the case of the recombinant proteins obtained by NASOFF et al., they are fusion proteins in which 308 amino acids, which are completely foreign to the CORE protein (SEQ ID NO:3), are present in the N-terminal position.

Although the authors stipulate that for the detection tests, the glutathione S-transferase part of the fusion protein does not disrupt the reaction since none of the sera tested reacts with isolated glutathione S-transferase (therefore no false positives), it appears difficult to admit that these 90% of fusion protein do not in any way interfere in the reactivity with the anti-HCV antibodies.

Indeed, the fact that the N-terminal part of the disclosed sequences is linked to the C-terminal part of the fusion protein contributes towards restricting the accessibility of this N-terminal region. In contrast, the C-terminal part is for its part detected. It is highly probable that it is these structural stresses, imposed by the production of a recombinant fusion protein in which the immunogenic part (the CORE part) represents the minor part of the fusion protein (less than 10% in this case), which lead to results contrary to those presented.

The amino acids are represented according to FIGS. 1 and 2, according to the convention of the Table below:

TABLE 6

| AMINO ACID | 3 LETTER CODE | MOLECULAR WEIGHT |
|---|---|---|
| ALANINE | Ala | 89 |
| CYSTEINE | Cys | 121 |
| ASPARTIC AC. | Asp | 133 |
| GLUTAMIC AC. | Glu | 147 |
| PHENYLALANINE | Phe | 165 |
| GLYCINE | Gly | 75 |

TABLE 6-continued

| AMINO ACID | 3 LETTER CODE | MOLECULAR WEIGHT |
|---|---|---|
| HISTIDINE | His | 155 |
| ISOLEUCINE | Ile | 131 |
| LYSINE | Lys | 146 |
| LEUCINE | Leu | 131 |
| METHIONINE | Met | 149 |
| ASPARGINE | Asn | 132 |
| PROLINE | Pro | 115 |
| GLUTAMINE | Gln | 146 |
| ARGININE | Arg | 174 |
| SERINE | Ser | 105 |
| THREONINE | Thr | 119 |
| VALINE | Val | 117 |
| TRYPTOPHAN | Trp | 204 |
| TYROSINE | Tyr | 181 |

According to the invention, the complete experimental procedure described above clearly demonstrates, by the types of antigen-antibody reaction carried out either in solid phase (direct ELISA, cf Table 2), or by inhibition (cf Table 3), that the sequence 2–45 of the CORE protein (SEQ ID NO:3) of the HCV virus obtained by solid phase chemical synthesis not only proves substantially greater than smaller sequences (S18D (SEQ ID NO:11) or V22G (SEQ ID NO:12)), but also that it exhibits a sensitivity equivalent to the CORE protein (SEQ ID NO:3) itself (protein C22-3 of the 2nd generation CHIRON RIBA HCV test), and that consequently the synthetic peptide S42G (SEQ ID NO:2) can be used in serological diagnostic tests in place of the CORE protein (SEQ ID NO:3).

It is evident from all these results that peptide S42G (SEQ ID NO:2) appears to be the minimum but sufficient structure which, from the point of view of its antigenic properties, is equivalent to the CORE protein (SEQ ID NO:3) in its entirety and can therefore replace it in a reagent for the detection of HCV.

What is claimed is:

1. A polypeptide that specifically binds to antibodies that specifically bind to human hepatitis C virus and that is selected from the group consisting of sequence SEQ ID NO:1 and sequence SEQ ID NO:2.

2. The polypeptide according to claim 1, consisting of sequence SEQ ID NO:1.

3. The polypeptide according to claim 1, consisting of sequence SEQ ID NO:2.

4. A reagent for detection of human hepatitis C virus, comprising as a reactive substance an isolated polypeptide according to claim 1.

5. The reagent according to claim 4, wherein said reagent is supported by a solid support.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 45 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
      (A) ORGANISM: Human Hepatitis C Virus
      (B) STRAIN: H77

(ix) FEATURE:
      (A) NAME/KEY: Peptide
      (B) LOCATION: 1..45

(D) OTHER INFORMATION: /note= "N-terminal sequence of the
            protein of the nucleocapside or CORE protein of the human
            hepatitis C virus"

(xi) SEQUENCE DESCRIPTION: SEQ ID NO:1:

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly
            35                  40                  45

(2) INFORMATION FOR SEQ ID NO:2:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Human Hepatitis C Virus
        (B) STRAIN: H77

(ix) FEATURE:
        (A) NAME/KEY: Peptide
        (B) LOCATION: 1..44
        (D) OTHER INFORMATION: /note= "N-terminal sequence of the
            protein of the nucleocapside or CORE protein of the human
            hepatitis C virus"

(xi) SEQUENCE DESCRIPTION: SEQ ID NO:2:

Ser Thr Asn Pro Lys Pro Gln Arg Lys Thr Lys Arg Asn Thr Asn Arg
1               5                   10                  15

Arg Pro Gln Asp Val Lys Phe Pro Gly Gly Gly Gln Ile Val Gly Gly
            20                  25                  30

Val Tyr Leu Leu Pro Arg Arg Gly Pro Arg Leu Gly
            35                  40

(2) INFORMATION FOR SEQ ID NO:3:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Human Hepatitis C Virus (xi) SEQUENCE DESCRIPTION: SEQ ID NO:3:

Met Ser Thr Asn Pro Lys Pro Gln Arg Lys Thr Lys Arg Asn Thr Asn
1               5                   10                  15

```
Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
             85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala
                180                 185                 190

(2) INFORMATION FOR SEQ ID NO:4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Human Hepatitis C Virus (xi) SEQUENCE DESCRIPTION: SEQ ID NO:4:

Lys Arg Asn Thr Asn Arg Arg Pro Gln Asp Val Lys Phe Pro Gly Gly
1                5                  10                  15

Gly Gln Ile Val Gly Gly Val Tyr
             20

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
```

```
            (A) ORGANISM: Human Hepatitis C Virus (xi) SEQUENCE DESCRIPTION: SEQ ID NO:5:

Pro Gln Arg Lys Thr Lys Arg Asn Thr Asn Arg Arg Pro Gln Asp Val
1               5                   10                  15

Lys Phe Pro Gly Gly Gly Gln Ile Val Gly Gly Val Tyr
            20                  25

(2) INFORMATION FOR SEQ ID NO:6:

(i) SEQUENCE CHARACTERISTICS:
         (A) LENGTH: 34 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: Human Hepatitis C Virus (xi) SEQUENCE DESCRIPTION: SEQ ID NO:6:

Ser Thr Asn Pro Lys Pro Gln Arg Lys Thr Lys Arg Asn Thr Asn Arg
1               5                   10                  15

Arg Pro Gln Asp Val Lys Phe Pro Gly Gly Gly Gln Ile Val Gly Gly
            20                  25                  30

Val Tyr (2) INFORMATION FOR SEQ ID NO:7:

(i) SEQUENCE CHARACTERISTICS:
         (A) LENGTH: 34 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
         (A) ORGANISM: Human Hepatitis C Virus (xi) SEQUENCE DESCRIPTION: SEQ ID NO:7:

Lys Arg Asn Thr Asn Arg Arg Pro Gln Asp Val Lys Phe Pro Gly Gly
1               5                   10                  15

Gly Gln Ile Val Gly Gly Val Tyr Leu Leu Pro Arg Arg Gly Pro Thr
            20                  25                  30

Leu Gly (2) INFORMATION FOR SEQ ID NO:8:

(i) SEQUENCE CHARACTERISTICS:
         (A) LENGTH: 39 amino acids
         (B) TYPE: amino acid
         (C) STRANDEDNESS: single
         (D) TOPOLOGY: linear
```

```
        (ii) MOLECULE TYPE: peptide (iii) HYPOTHETICAL: NO (iv) ANTI-SENSE: NO (v) FRAGMENT TYPE: N-terminal (vi) ORIGINAL SOURCE:
             (A) ORGANISM: Human Hepatitis C Virus (xi) SEQUENCE DESCRIPTION: SEQ ID NO:8:

Pro Gln Arg Lys Thr Lys Arg Asn Thr Asn Arg Arg Pro Gln Asp Val
1               5                  10                  15

Lys Phe Pro Gly Gly Gly Gln Ile Val Gly Val Tyr Leu Leu Pro
            20                  25                  30

Arg Arg Gly Pro Arg Leu Gly
        35

(2) INFORMATION FOR SEQ ID NO:9:

(i) SEQUENCE CHARACTERISTICS:
             (A) LENGTH: 44 amino acids
             (B) TYPE: amino acid
             (C) STRANDEDNESS: single
             (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
             (A) ORGANISM: Human Hepatitis C Virus (xi) SEQUENCE DESCRIPTION: SEQ ID NO:9:

Pro Arg Arg Gly Pro Arg Leu Gly Val Arg Ala Thr Arg Lys Thr Ser
1               5                  10                  15

Glu Arg Ser Gln Pro Arg Gly Arg Arg Gln Pro Ile Pro Lys Ala Arg
            20                  25                  30

Arg Pro Glu Gly Arg Thr Trp Ala Gln Pro Gly Tyr
        35                  40

(2) INFORMATION FOR SEQ ID NO:10:

(i) SEQUENCE CHARACTERISTICS:
             (A) LENGTH: 42 amino acids
             (B) TYPE: amino acid
             (C) STRANDEDNESS: single
             (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
             (A) ORGANISM: Human Hepatitis C Virus (xi) SEQUENCE DESCRIPTION: SEQ ID NO:10:

Arg Thr Trp Ala Gln Pro Gly Tyr Pro Trp Pro Leu Tyr Gly Asn Glu
1               5                  10                  15

Gly Cys Gly Trp Ala Gly Trp Leu Leu Ser Pro Arg Gly Ser Arg Pro
```

```
                        20                  25                  30
Ser Trp Gly Pro Thr Asp Pro Arg Arg Arg
            35                  40
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Human Hepatitis C Virus (xi) SEQUENCE DESCRIPTION: SEQ ID NO:11:

```
Ser Thr Asn Pro Lys Pro Gln Arg Lys Thr Lys Arg Asn Thr Asn Arg
1               5                   10                  15
Arg Pro Gln Asp
            20
```

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Human Hepatitis C Virus (xi) SEQUENCE DESCRIPTION: SEQ ID NO:12:

```
Val Lys Phe Pro Gly Gly Gly Gln Ile Val Gly Gly Val Tyr Leu Leu
1               5                   10                  15
Pro Arg Arg Gly Pro Arg Leu Gly
            20
```